(12) United States Patent
Youssefi et al.

(10) Patent No.: US 7,895,011 B2
(45) Date of Patent: Feb. 22, 2011

(54) METHOD AND APPARATUS FOR PERFORMING REMOTE CALIBRATION VERIFICATION

(75) Inventors: Gerhard Youssefi, Landshut (DE); Julia Hoff, Munich (DE); Anton Hilger, Munich (DE); Michael L. Kliewer, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 85 days.

(21) Appl. No.: 12/336,893

(22) Filed: Dec. 17, 2008

(65) Prior Publication Data

US 2010/0153047 A1 Jun. 17, 2010

(51) Int. Cl.
*G06F 11/30* (2006.01)

(52) U.S. Cl. .................................. 702/108; 702/85

(58) Field of Classification Search ............ 702/85, 702/108, 138, 151, 183; 324/74, 130; 709/224
See application file for complete search history.

(56) References Cited

U.S. PATENT DOCUMENTS

| | | | |
|---|---|---|---|
| 5,798,518 A | 8/1998 | Coleman | |
| 6,022,109 A | 2/2000 | Dal Santo | |
| 6,487,513 B1 * | 11/2002 | Eastvold et al. | 702/108 |
| 6,637,884 B2 | 10/2003 | Martino | |
| 6,647,885 B2 | 11/2003 | Murata et al. | |
| 6,996,487 B2 | 2/2006 | Jutras et al. | |
| 7,062,397 B1 | 6/2006 | Minor | |
| 7,209,847 B2 | 4/2007 | Kobayashi | |
| 7,213,919 B2 | 5/2007 | Persoff | |
| 7,227,810 B2 | 6/2007 | Ito | |
| 2007/0203873 A1 | 8/2007 | Jeunink et al. | |
| 2007/0208244 A1 | 9/2007 | Brauker | |
| 2008/0208018 A1 | 8/2008 | Ridder | |

FOREIGN PATENT DOCUMENTS

WO WO 92/01264 A1 1/1992
WO WO 2006/123186 A1 11/2006

OTHER PUBLICATIONS

ACTEL, "Silicon Sculptor Verification of Calibration Work Instruction," Nov. 2007, (p. 1-7).
International Search Report (PCTISA/210) and Written Opinion (PCT/ISA/237) mailed on May 4, 2010.
9932 Calibrate-IT, "User's Guide," Hart Scientific Rev. 142501, 1998-2001, (p. 6-7).

* cited by examiner

*Primary Examiner*—John H Le
(74) *Attorney, Agent, or Firm*—Jeffrey B. Powers (57) ABSTRACT

A method and apparatus for remotely verifying the calibration status of a diagnostic instrument, for example, following remote installation of a software upgrade on the instrument. In one example, a method of verifying the calibration status of the instrument, includes retrieving stored raw calibration test data generated during a previously-performed calibration of the instrument, processing the raw calibration test data to generate a diagnostic reading, comparing the diagnostic reading to a known nominal reading, and based on the comparison, generating an output indicative of the calibration status of the instrument. In one example, the method is performed without contemporaneously measuring a calibration object with the instrument and therefore, without activating the measurement head or measurement optics of the instrument.

21 Claims, 10 Drawing Sheets

METHOD AND APPARATUS FOR PERFORMING REMOTE CALIBRATION VERIFICATION

BACKGROUND

1. Field of Invention

The present invention relates generally to servicing of diagnostic systems and, more particularly, to verifying the calibration status of a diagnostic system.

2. Discussion of Related Art

For current existing diagnostic systems such as, for example, optical diagnostic systems such as wavefront sensors or corneal topography systems, calibration objects are used to perform and test the hardware and software calibration of the diagnostic system. These calibration objects are standardized devices having accurately known characteristics. In general the calibration procedure requires a trained operator who mounts and aligns the calibration objects in or on the diagnostic system being calibrated.

Figure 1:
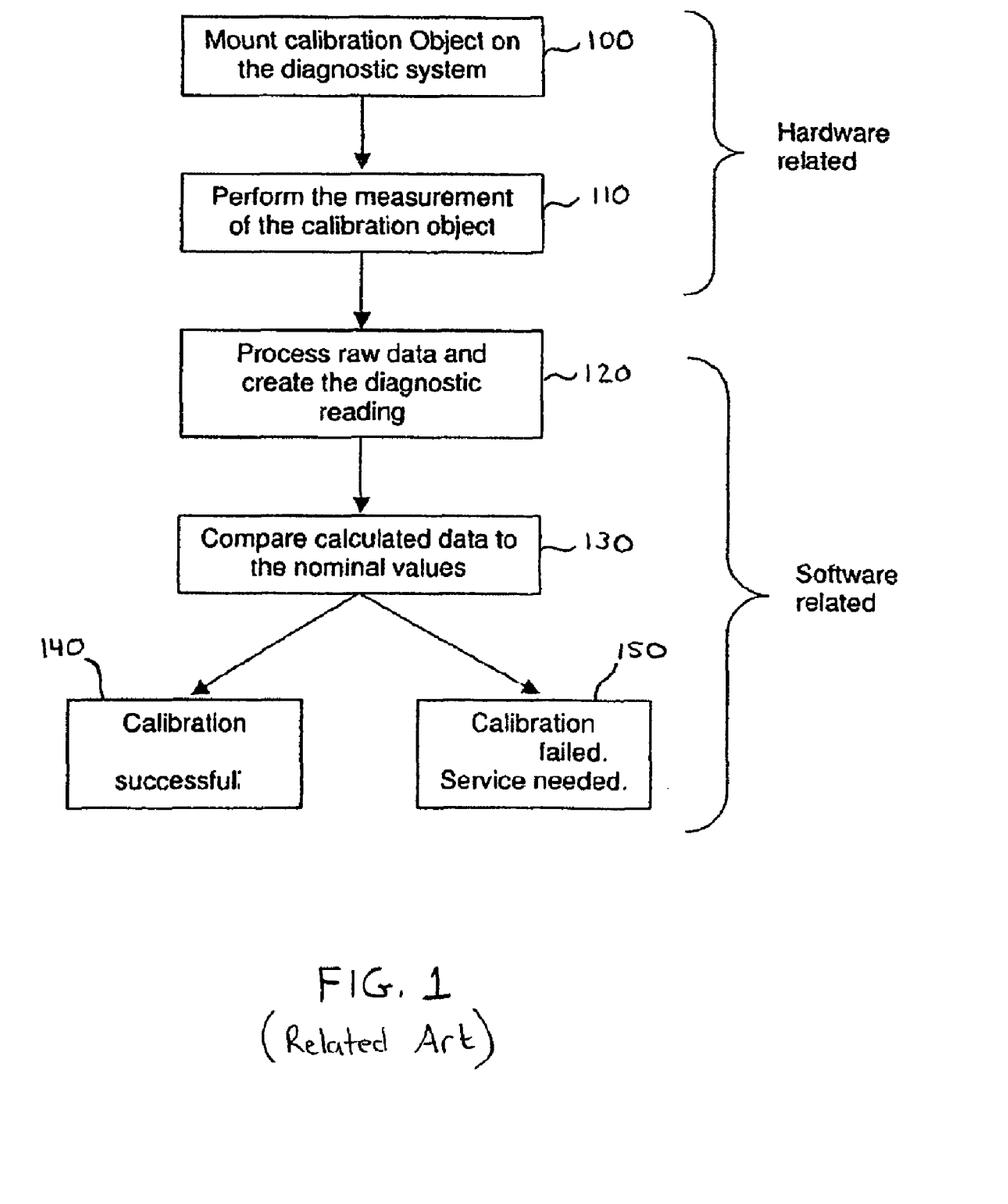
FIG. 1 is a flow diagram of a conventional calibration procedure.

Referring to FIG. 1, there is illustrated a flow diagram of a calibration procedure for a diagnostic system. First, in step 100, a calibration object is mounted and aligned on or in front of the measurement head of the diagnostic system. After correct alignment of the calibration object, a measurement of the calibration object is performed (step 110). This step 110 is referred to as an acquisition since data is acquired from the measurement. In step 120, the collected data are processed to create a diagnostic reading. This diagnostic reading is then compared with expected results based on the known characteristics of the calibration object (step 130). Based on the result of this comparison, the operator is able determine either than the calibration was successful (step 140) or that the calibration failed, indicating a problem with either the calibration object or the diagnostic system (step 150).

SUMMARY OF INVENTION

Aspects and embodiments are directed to methods and apparatus to facilitate remote servicing of diagnostic devices, particularly, to remotely verify the software calibration of a diagnostic device following a software upgrade or other remote service operation. By providing the ability to remotely (i.e., from a location other than the location of the diagnostic device) verify the calibration status, the usefulness and efficiency of remote software service of diagnostic systems may be enhanced.

One embodiment is directed to a method of remotely updating and verifying a calibration status of an instrument that comprises a measurement portion and a computer system coupled to the measurement portion. In one example, the instrument is a diagnostic system. The method comprises acts of providing a software update to the instrument from a remote location via a communications link, without activating the measurement portion of the instrument, performing a calibration check procedure at the instrument, and providing a calibration status indicator that identifies the calibration status of the instrument following the calibration check procedure. In one example, performing the calibration check procedure is done without contemporaneously activating the measurement portion of the instrument. In another example, performing the calibration check procedure does not include contemporaneously measuring a calibration object with the instrument.

According to one example, performing the calibration check procedure includes retrieving stored calibration test data, processing the calibration test data to generate a diagnostic reading, comparing the diagnostic reading to a known correct nominal reading, and based on the comparison, generating the calibration status indicator. Performing the calibration check procedure may further comprise retrieving stored calibration parameters, wherein processing the calibration test data is performed using the calibration parameters. Retrieving the stored calibration test data includes retrieving a stored digital image. According to another example, performing the calibration check procedure includes retrieving stored raw calibration test data, processing the raw calibration test data to generate a diagnostic reading, comparing the diagnostic reading to a known correct nominal reading, and based on the comparison, generating the calibration status indicator. Retrieving the stored raw calibration test data may include retrieving a stored digital image. Performing the calibration check procedure may further comprise retrieving stored calibration parameters, wherein processing the raw calibration test data is performed using the calibration parameters. In one example, generating the calibration status indicator includes generating the calibration status indicator that indicates that the calibration status of the instrument is non-operational. Generating the calibration status indicator may include generating data that identifies one or more corrupted calibration parameters. Generating the calibration status indicator may include generating a calibration status indicator that indicates that the calibration status of the instrument is operational. In one example, providing the calibration status indicator includes providing the calibration status indicator from the instrument via the communications link. In another example, providing the calibration status indicator includes providing the calibration status indicator from the instrument to a remote user interface via the communications link.

Another embodiment is directed to a method of verifying a calibration status of an instrument comprising a processor, the method comprising acts of initiating a calibration check procedure on the processor, retrieving stored raw calibration test data obtained during a previously-performed calibration procedure on the instrument, processing the raw calibration test data with the processor to generate a diagnostic reading, and based on the diagnostic reading, generating a calibration status indicator that indicates whether the calibration check procedure passed or failed.

In one example of the method, generating the calibration status indicator includes an act of comparing the diagnostic reading to a known nominal reading and generating the calibration status indicator based on a result of the comparing act. In another example, processing the raw calibration test data includes processing the raw calibration test data using calibration parameters specific to the instrument. In another example, retrieving the stored raw calibration test data includes retrieving a digital image of a calibration test object taken by the instrument during the previously-performed calibration procedure. The method may further comprise an act of providing the calibration status indicator to a remote user interface via a communication link between the instrument and the remote user interface. In one example, verifying of the calibration status of the instrument is performed without contemporaneously measuring a calibration object with the instrument.

According to another embodiment, a method of verifying a calibration status of an instrument comprising acts of retrieving stored calibration test data, processing the calibration test data to generate a diagnostic reading, comparing the diagnostic reading to a known nominal reading, and based on the comparison, generating an output indicative of the calibration status of the instrument, wherein the verifying of the calibration status of the instrument is performed without measuring a calibration object with the instrument. In one example, retrieving the stored calibration test data and processing the calibration test data to generate the diagnostic reading comprises retrieving stored raw calibration test data, and processing the raw calibration test data to generate the diagnostic reading. In another example, verifying of the calibration status of the instrument is performed without contemporaneously measuring a calibration object with the instrument. Retrieving the stored calibration test data may include retrieving a stored digital image. Processing the calibration test data may include processing the calibration test data using calibration parameters specific to the instrument. In one example, processing the raw calibration test data includes processing the raw calibration test data using calibration parameters specific to the instrument. Generating the output indicative of the calibration status of the instrument may include generating an output that identifies a corrupted calibration parameter. In another example, generating the output indicative of the calibration status of the instrument includes generating an output that indicates instrument maintenance is required. In another example, generating the output indicative of the calibration status of the instrument includes generating an output that indicates that the instrument is properly calibrated.

According to another embodiment, a diagnostic system comprises a measurement portion, a computer system coupled to the measurement portion, and a communications link coupled to the computer system, wherein the computer system comprises a processor configured to receive a software update from a remote location via the communications link, to perform a calibration check procedure of the diagnostic system without activating the measurement portion, and to provide a calibration status indicator that identifies the calibration status of the diagnostic system following the calibration check procedure. In one example, the processor is configured to verify of the calibration status of the diagnostic system without contemporaneous measurement of a calibration object with the measurement portion. In one example, the processor is further configured to provide the calibration status indicator to a remote user interface via the communications link. In another example, the computer system further comprises a storage device, and the processor is configured to perform the calibration check procedure by retrieving stored raw calibration test data from the storage device, processing the raw calibration test data to generate a diagnostic reading, comparing the diagnostic reading to a known nominal reading, and based on the comparison, generating the calibration status indicator.

According to another embodiment, a diagnostic system comprises a measurement head, a storage device coupled to the measurement head and which stores raw calibration test data generated by the measurement head, and a processor coupled to the storage device. The processor is configured to retrieve the stored raw calibration test data from the storage device without activating the measurement head, to process the raw calibration test data to generate a diagnostic reading, to compare the diagnostic reading to a known nominal reading, and based on the comparison, to generate an output indicative of a calibration status of the diagnostic system. Thus, the processor may be configured to verify a calibration status of the diagnostic system without requiring contemporaneous measurement of a calibration object with the measurement head.

In one example, the diagnostic system further comprises a communications port coupled to a communications link and to the processor, wherein the processor is further configured to transmit the output to a remote location via the communications link. In another example, the processor is further configured to receive a software upgrade via the communications link and to initiate a calibration check procedure following installation of the software upgrade. The diagnostic system may comprise, for example, at least one of a pupilometer, a wavefront sensor, a placido device and a slit scan device. In one example, the storage device stores calibration parameters specific to the diagnostic system, and the processor is further configured to retrieve at least one calibration parameter from the storage device and to process the raw calibration test data using the at least one calibration parameter to generate the diagnostic reading. In one example, the output indicates that the calibration status of the diagnostic system is invalid, and contains information indentifying at least one corrupted calibration parameter. In another example, the stored raw calibration test data includes a stored digital image of a calibration object. The digital image may be acquired during a calibration measurement performed prior to the calibration check procedure.

According to another embodiment, computer-readable media having computer-readable signals stored thereon that define instructions which, as a result of being executed by a computer or processor, instruct the processor to perform a method for verifying the calibration status of an instrument are provided. The computer-readable media include separate computer-readable media with signals stored thereon for performing each individual element of the methods described above, and computer-readable media for performing the method elements described above in combination.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment in any manner consistent with the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. Where technical features in the figures, detailed description or any claim are followed by references signs, the reference signs have been included for the sole purpose of increasing the intelligibility of the figures, detailed description, and/or claims. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure. In the figures:

DETAILED DESCRIPTION

Figure 2:
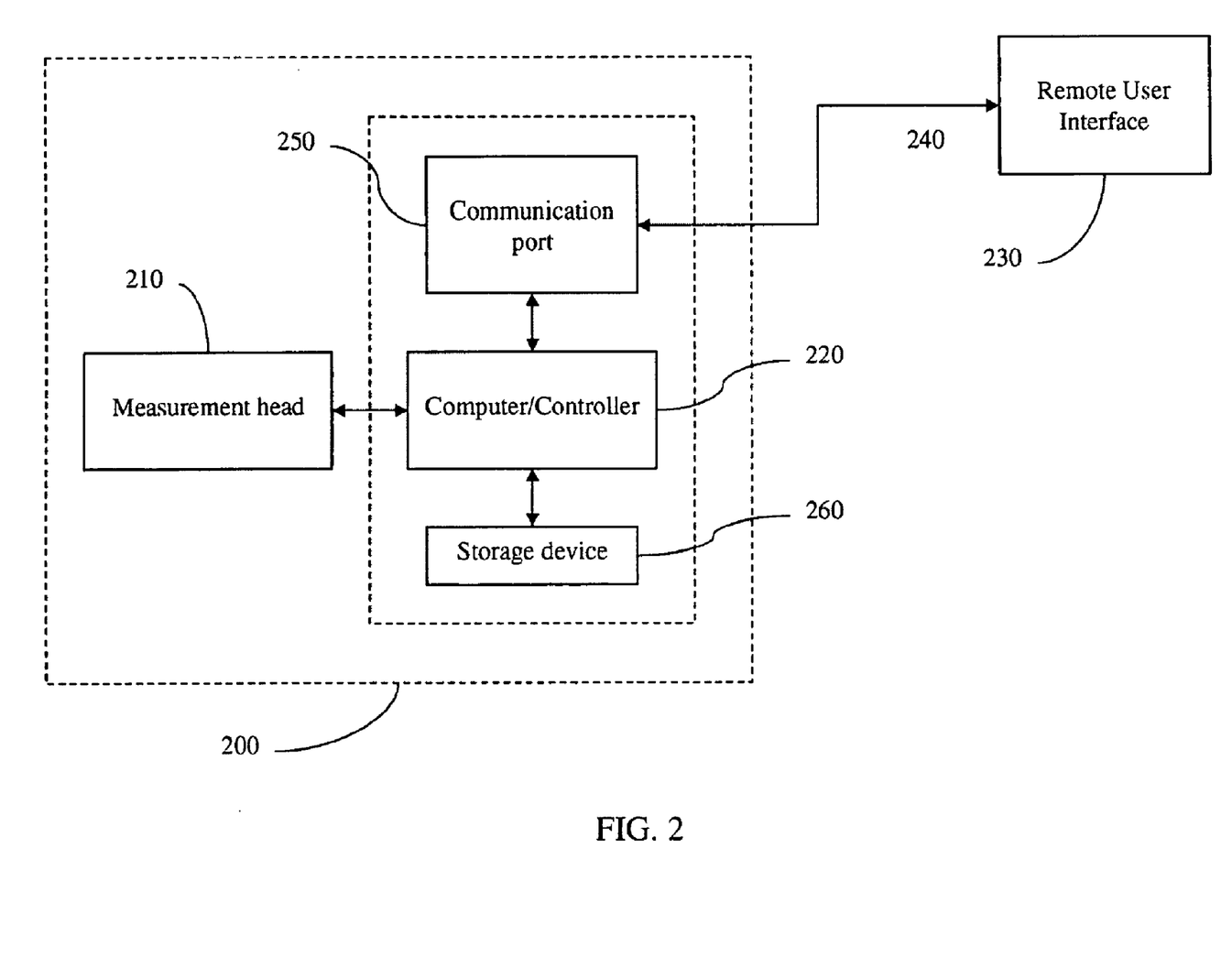
FIG. 2 is a block diagram of one example of a diagnostic system according to aspects of the invention.
Figure 3:
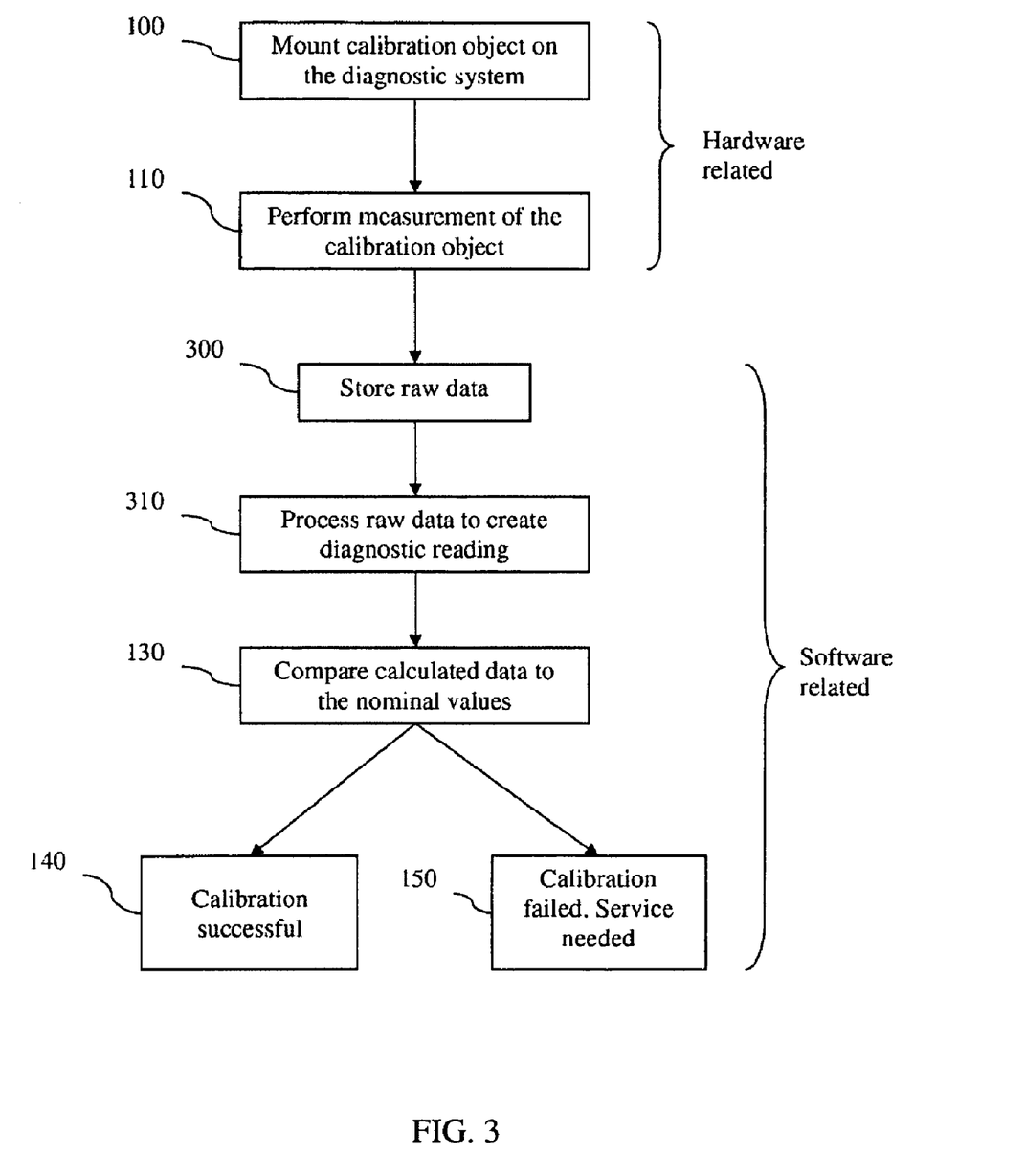
FIG. 3 is a flow diagram of one example of a calibration or calibration verification procedure, according to aspects of the invention.

Diagnostic systems generally include both hardware and software portion. As illustrated in FIG. 3, the hardware of the diagnostic system 200 includes a measurement head 210 that performs measurements on test objects or calibration objects mounted on the system, and a computer or processor 220. The computer 220 may be implemented in a variety of ways, including, but not limited to, a general purpose computer coupled to the measurement head 210, and an integrated specialized computer. The computer 220 is programmed with software that may perform or control various aspects and functions of the diagnostic system, including, for example, processing software to analyze the data acquired during such a measurement and to generate the diagnostic reading. This software may be periodically updated as part of the maintenance of the diagnostic system. According to one embodiment, the diagnostic system 200 is coupled to user interface at a remote location 230 via a communications link 240 to allow remote upgrades or updates of the software to be performed via the communications link 240. Thus, the computer 220 may include or be coupled to a communications port 250. Examples of the communications link 240 include, but are not limited to, a wireless link, a wired link, a fiber optic link, an Internet connection, a network connection, etc. Similarly, the communications port 250 may be implemented using standard systems.

As discussed above, typical calibration procedures for such diagnostic systems include the mounting of calibration objects on the diagnostic system and comparing the data from a measurement of the calibration object with the nominal values. During the calibration procedure, the unique hardware configuration of the diagnostic system is included in the calculation of a measurement analysis. If the calculated values, or diagnostic reading, obtained from the measurement analysis are within a certain acceptance range, then the diagnostic system is considered to be appropriately calibrated, while any deviation from the acceptance range indicates that the calibration status is no longer valid. The acceptance range may be defined by ranges of accepted values for each of a variety of calibration parameters. These calibration parameters depend on the diagnostic system and may include, for example, parameters such as the pixel size of the camera, the focal length of the camera, the distance between mirrors, etc., as known to those skilled in the art.

Since the calibration parameters are stored in the software of the diagnostic system, it is possible that when a software upgrade is installed, the calibration parameters may be corrupted. Accordingly, when the software is updated, it is important to verify the calibration status of the diagnostic device. As discussed above, diagnostic systems can be communicatively coupled to remote locations, such that remote software updates can be performed. However, as also discussed above, conventional calibration procedures generally require a trained operator to mount and align the calibration object on the diagnostic system. Therefore, even though the software update can be installed remotely, complete software servicing of the diagnostic system requires an on-site operator to verify the calibration.

According to one embodiment, by providing a method and apparatus to remotely verify the calibration status of a diagnostic system, the base for a remote software service is opened. As discussed further below, aspects and embodiments avoid the need for having an operator at the diagnostic system to check the calibration status locally whenever a software upgrade is remotely installed. In addition, embodiments of the methods and apparatus discussed herein may be used to perform calibration status checks at any time, for example, on a regular basis to detect unintended changes in the diagnostic system, or after events, such as a power failure, or at any other time when verification of the calibration status of the diagnostic system is desired.

It is to be appreciated that embodiments of the methods and apparatus discussed herein are not limited in application to the details of construction and the arrangement of components set forth in the following description or illustrated in the accompanying figures. The methods and apparatus are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, and upper and lower are intended for convenience of description, not to limit the present systems and methods or their components to any one positional or spatial orientation.

Referring to FIG. 3, there is illustrated a flow diagram of one example of a calibration or calibration verification procedure similar to the calibration procedure discussed above with reference to FIG. 1. According to one embodiment, when the measurement of the calibration object is performed (step 110), raw digital data is acquired. Step 300 includes storing this acquired raw data, referred to as raw calibration test data, in a storage device or memory device 260 forming part of or coupled to the computer 220 of the diagnostic system 200 (see FIG. 2). In one example, in which the diagnostic system is an optical system configured to measure the human eye, the calibration objects for each individual diagnostic system are designed to model the applicable characteristics of a real eye. Accordingly, the typical data collected during an acquisition is not significantly different from data originating from a real eye. In one example, the raw data acquired during step 110 are images taken by cameras (included in the measurement head 210) which operate either in the visible or the infrared range of the spectrum. Thus, the raw data may include color images or greyscale images that may be stored as digital data. Similarly, in other examples in which the diagnostic systems analyze things other than the eye, (e.g., spectrum analyzers, spectrometers, etc.), the acquired raw data may be images or numeric data that can be stored as digital data. Accordingly, although the following discussion may refer to examples of optical diagnostic systems, it is to be appreciated that the invention is not so limited and may be applied to any type of diagnostic system in which digital data is acquired during the calibration procedure.

Still referring to FIG. 3, in step 310 the processing software processes the acquired images and the outcome of the analysis is a set of values which are used to either calibrate or determine the calibration status of the system. As discussed above, the measurement of the calibration object (step 110) includes the unique hardware configuration of the diagnostic system. Accordingly, steps 100 and 110 are "hardware related" in that they rely on and incorporate aspects of the measurement head 210. If no changes are made to the hardware, for example, only a software update is performed, then the hardware-related parts of the calibration procedure (steps 100 and 110) should be stable within the established maintenance interval for the diagnostic system.

Accordingly, in one embodiment, a method of verifying the calibration status of a diagnostic system is independent of the hardware-related portions of a conventional calibration procedure and therefore, may be performed remotely. According to one embodiment, the method uses raw calibration test data from a previously performed calibration procedure that was stored in storage device 260 during step 300 in conjunction with the stored calibration parameters to verify whether the calibration status of the diagnostic system is valid, or whether an event (such as corruption of one or more calibration parameters during a software upgrade) has invalidated the calibration status of the system.

Figure 4:
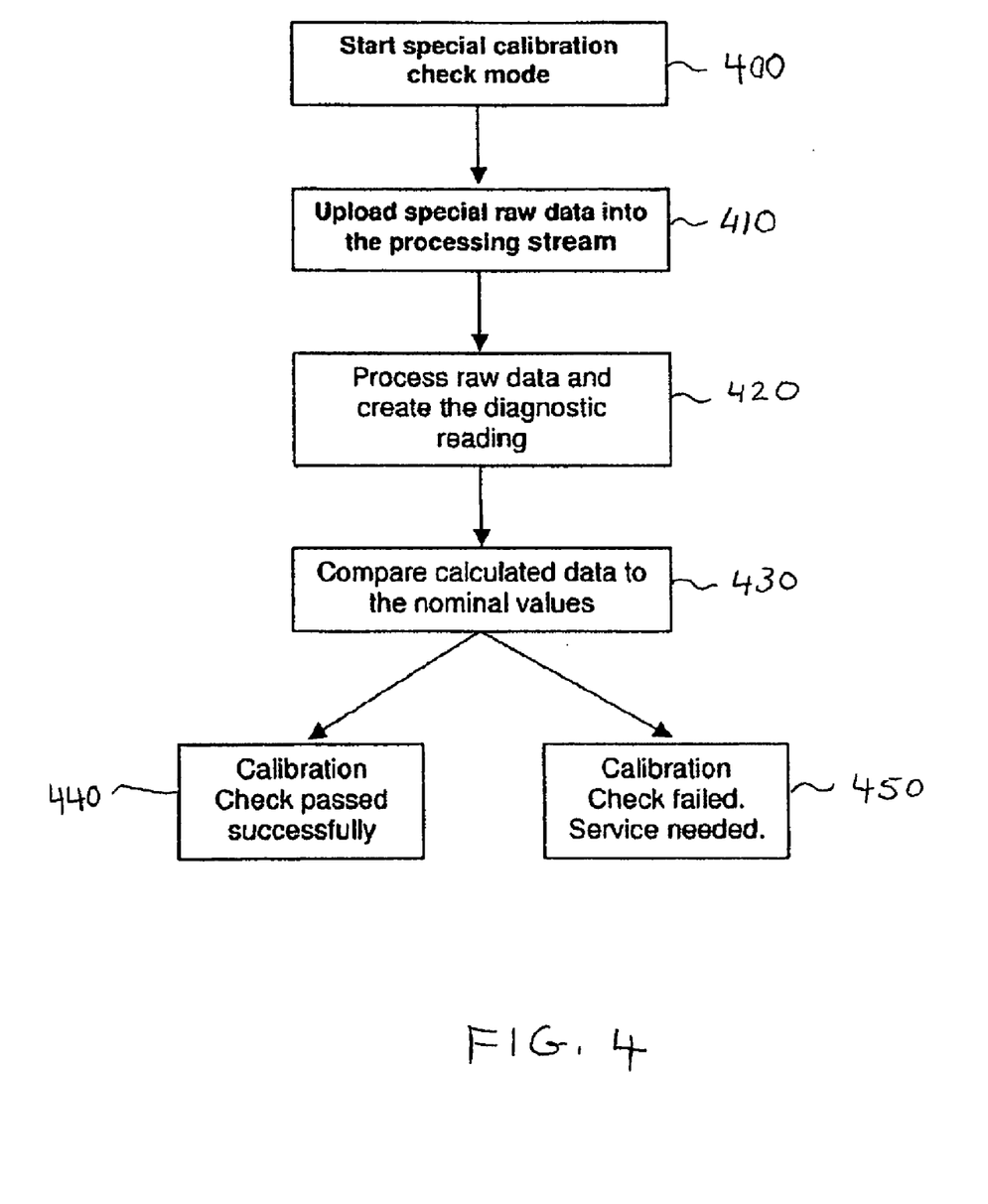
FIG. 4 is a flow diagram of one example of a remote calibration verification procedure according to aspects of the invention.

Referring to FIG. 4, there is illustrated a flow diagram of one example of a method for verifying the calibration status of a diagnostic system. In step 400, the diagnostic system enters a calibration check mode to perform the calibration check procedure. The calibration check mode may be initiated, for example, by a command issued to the computer 220 from the remote user interface 230. The command to initiate the calibration check procedure may be issued responsive to a condition or event such as, but not limited to, following a software upgrade installed on the diagnostic system, a power failure at the location of the diagnostic system, a crash of the computer 220, or as part of a routine maintenance event. In another example, the calibration check mode may be entered automatically based on policies, such as maintenance schedule, stored on the computer 220 or automatically transmitted to the computer 220 via the communications link 240.

Once the calibration check procedure is initiated, the processing software uploads the stored raw data set and the stored calibration parameters into the processing stream (step 410). This makes the mounting of a calibration object obsolete. Accordingly, in one example, steps 100 and 110 of a conventional calibration procedure are replaced with steps 400 and 410 of the calibration check procedure. The stored raw data set is processed based on the stored calibration parameters to generate a diagnostic reading (step 420). If the calibration parameters are correct, assuming no other errors in the processing software, the diagnostic reading will correspond to a known set of outcomes. In this case, comparing the calculated diagnostic reading with known correct nominal values (step 430) will yield an expected result, and the processing software generates a calibration status indicator indicating that the calibration check passed successfully (step 440). Alternatively, if any of the calibration parameters are corrupted, or another error has occurred in the processing software, the result of step 430 will indicate that the diagnostic reading is outside of the defined acceptance range. In this case, the processing software generates a calibration status indicator that indicates that the calibration check has failed, i.e., the calibration status of the diagnostic system is invalid or non-operational, and accordingly, service of the diagnostic system may be required (step 450).

According to one embodiment, the computer 220 sends the calibration status indicator to the remote user interface 230 via the communications link 240. Thus, the calibration check procedure may be initiated remotely and the result of the procedure may be viewed remotely. Furthermore, the calibration check procedure does not require a calibration object to be mounted on the diagnostic system and does not require the measurement head of the instrument to be activated. Therefore, the calibration check procedure may be performed without an on-site operator present, and only the portions of the computer 220 required to access the storage device, perform the data processing, and transmit the calibration status indicator to the remote location need be active. Thus, embodiments of the method and apparatus allow an operator to perform a remote calibration test of the software components of the diagnostic device. This may greatly enhance the value of performing remote software upgrades to the diagnostic device since the calibration verification can also be done remotely, and may provide a solid regulatory base for remotely upgrading the software of diagnostic devices. Furthermore, the ability to remotely verify the calibration status of the instrument following a software upgrade or other event may greatly reduce the cost of these activities and of the maintenance of the instrument since the need for a local, trained operator to perform the calibration is avoided.

In addition, when the calibration check procedure fails, the calibration status indicator may contain information that allows a remote operator to diagnose what type of error has occurred, or which calibration parameter has been corrupted. This may allow the remote operator to initiate appropriate maintenance and direct an appropriate technician to service the instrument more quickly and more cost effectively. In particular, certain calibration parameters are directly related to recognizable features in the processed images or data streams. Accordingly, a change in one of these recognizable features may indicate to the operator which calibration parameter has been affected. For example, in an optical imaging system, the distance between the camera and the calibration object results in defocusing or magnetization of the entire image. Accordingly, if the processed image resulting from step 420 is either out of focus or enlarged/reduced in size compared to the expected result, this may indicate to the operator that the distance calibration parameter is corrupted.

In one example, the computer 220 may transmit the processed data to the remote user interface to be analyzed by the remote operator. Thus, the calibration status indicator may include the processed data. In another example, the processing software may identify candidate corrupted calibration parameters based on the result of the comparison step 403, and the calibration status indicator may include information identifying the candidate corrupted parameters. As will be recognized by those skilled in the art given the benefit of this disclosure, there are numerous variations on the information and data that may included in the calibration status indicator, including simply an indication that the calibration status is either valid/operational or invalid/non-operational. Furthermore, in one example, the calibration status indicator, optionally including the processed image, may be displayed locally by the computer 220 as well as, or instead of, being transmitted to the remote location. Similarly, the computer 220 may store the calibration status indicator for later access by a local operator.

In one embodiment, the raw data sets and calibration parameters are renewed and updated with each service action performed on-site by service personnel. For example, the raw data sets and/or calibration parameters may be updated when changes to the system hardware are made or during regular maintenance of the system. The raw data sets may also be updated when an operator performs a manual calibration of the diagnostic system, whether part of routine maintenance or not. Updating the stored raw data sets and calibration parameters may ensure that the remote software calibration checks are valid and accurate because current data is used. Furthermore, the use of digital data, rather than a physical calibration object, to perform the calibration check procedure may offer several advantages. For example, the characteristics of calibration objects may vary with changing environmental conditions, such as temperature or humidity; whereas stored digital data remains constant over time. In addition, various methods exist for verifying that digital data has in fact remained the same over time, such as, for example, checksum or other procedures. Accordingly, a more accurate calibration check result may be obtained using the stored digital data rather than a physical calibration object.

Embodiments of the calibration check procedure and method may be used for a variety of different measurement concepts and applied to many different diagnostic systems. The following examples serve to illustrate some of the novel features, aspect and examples of the technology disclosed herein and should not be construed as limiting the scope of the appended claims.

EXAMPLE 1

Figure 5A:
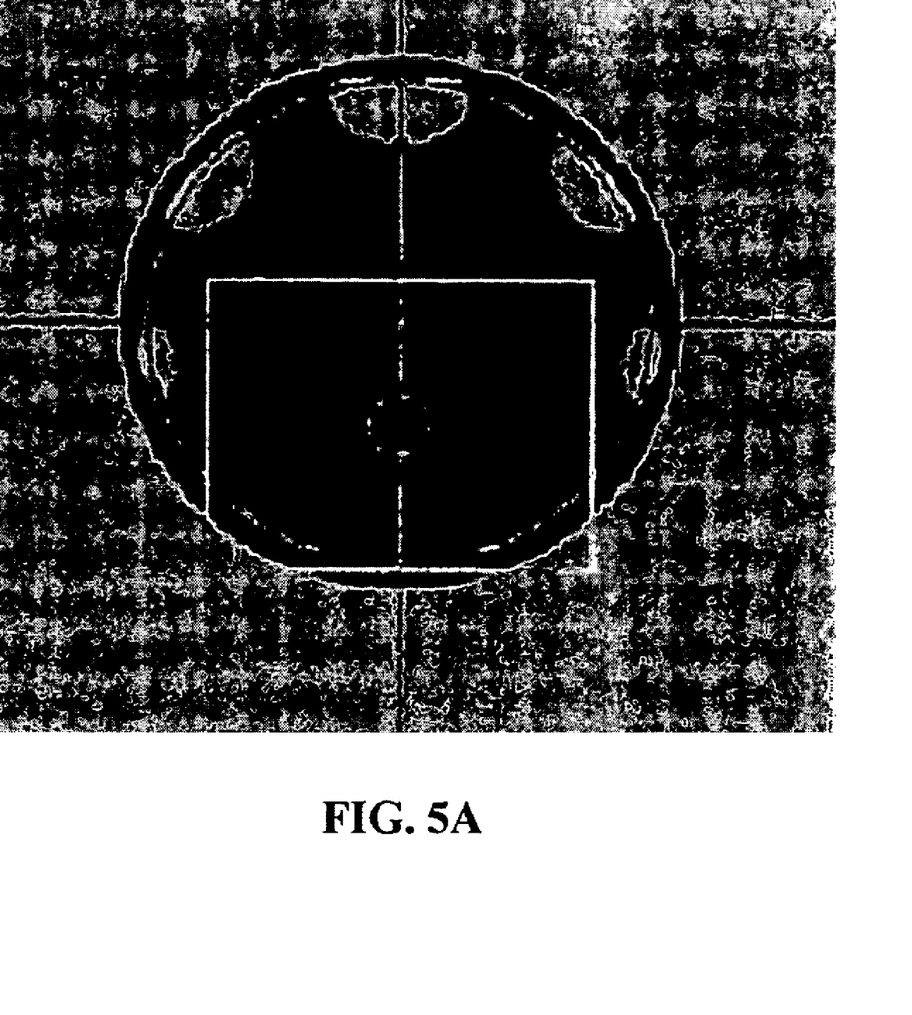
FIG. 5A is an example of a raw image of a pupil having a defined aperture size of 5 mm.

In one example, the calibration check procedure and method can be applied to a pupilometer. The reference of the pupilometer is set via a pupil image of a calibration object with a defined aperture. Accordingly, after the alignment of the appropriate calibration object in front of the pupilometer, the image illustrated in FIG. 5A is acquired using the pupil camera. FIG. 5 is an image of the pupil size (aperture size) for a calibration object with a defined aperture size of 5 mm. This image is the raw data set that is stored as digital data in step 300. As the size of the physical aperture of the calibration object is known, the analysis of the image needs to provide the specified size. Assuming that the calibration object is positioned correctly, any deviation from this predefined size indicates a problem, for example, wrong configuration of a calibration parameter.

One example of a pupilometer calibration parameter is the camera pixel to millimeter adjustment factor. Camera images are typically analyzed in pixel coordinates, thus the first information about the pupil diameter will be given in terms of the number of pixels ($N_{pix}$) inside the pupil. To determine the physical pupil size in millimeters, the camera-specific pixel-to-mm conversion factor (Pix2 mm) is utilized. This conversion factor is an example of a system calibration parameter which is given for any particular system and defined at the production of the system. Any software changes to the system should not modify this parameter. However, as discussed above, it is possible that this calibration parameter may be overwritten by a wrong value during a software upgrade. Corrupting this calibration parameter would lead to incorrectly concluded pupil diameters.

Accordingly, in one example, a remote calibration check may be used for verification of this calibration parameter which defines the number of μm per camera pixel. For a remote calibration check of the pupilometer, the digital raw data set corresponding to the pupil camera image of FIG. 5A is uploaded into the processing stream (step 410). In the processing step 430, the aperture size is calculated and, in the analysis step 440, the calculated aperture size is compared to the predefined expected value. For example, where the nominal pupil diameter $\emptyset_{nom}$ is known, the calibration check procedure can be used to determine the number of pixels, and by applying the Pix2 mm calibration parameter, will calculate the actual pupil diameter, $\emptyset_{act}$ using the equation:

$$\emptyset_{act} = N_{pix} \times \text{Pix2mm} \tag{1}$$

A comparison between $\emptyset_{act}$ and $\emptyset_{nom}$ during step 420 may lead to a conclusion about the status of the system calibration parameter Pix2 mm. Thus, step 430 of generating the calibration status indicator may include generating a status indicator that indicates whether or not the Pix2 mm calibration parameter is correct or not.

Figure 5B:
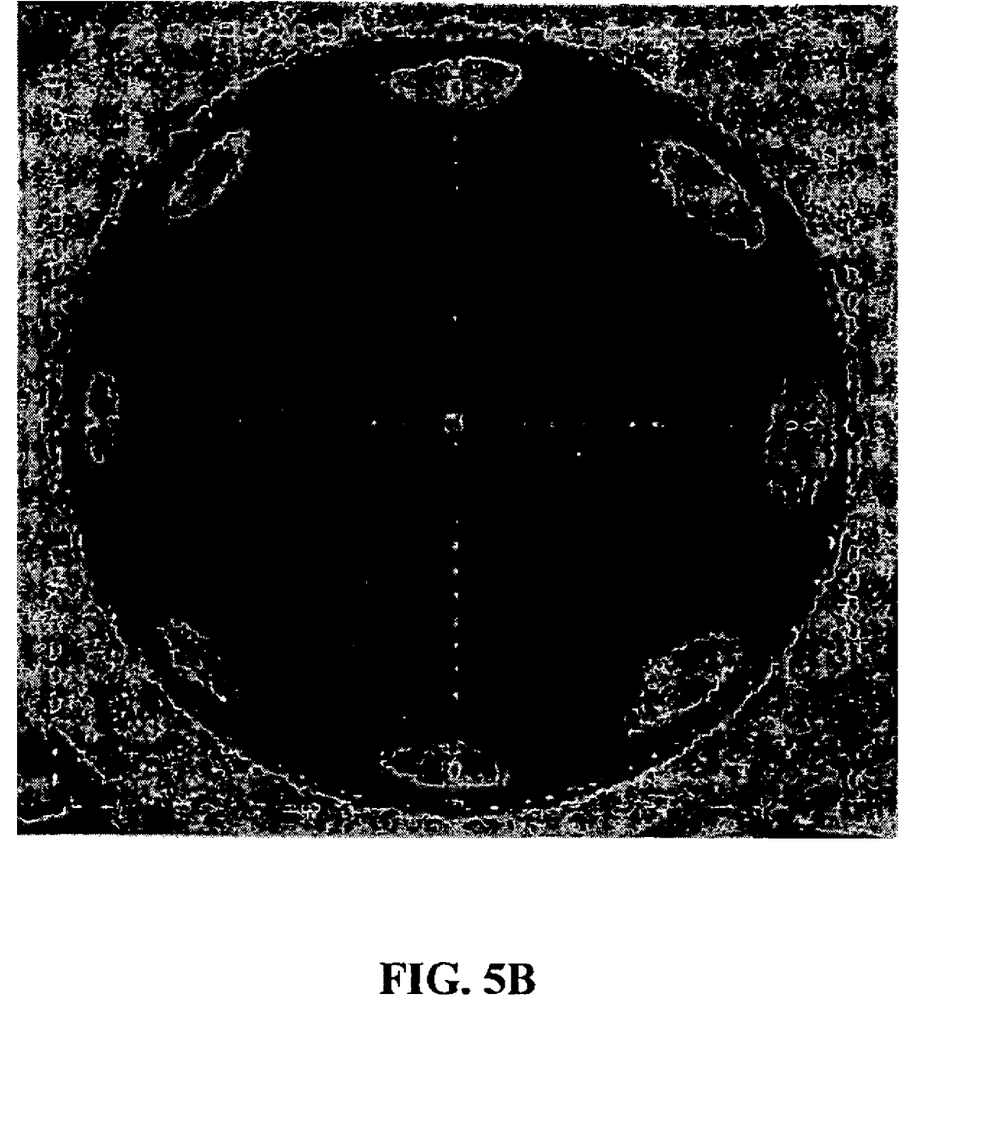
FIG. 5B is an example of a processed image corresponding to the raw image of FIG. 5A.

Additionally, if the calibration is correct, the processed image will resemble that shown in FIG. 5B, which is an image of a correctly adjusted pupil circle. As discussed above, following step 430, a calibration status indicator is generated, indicating either that the calibration status of the pupilometer is operational (step 440) or non-operational (step 450), and is saved on the computer 220, transmitted to the remote user interface 230, and/or locally displayed by the computer 220.

EXAMPLE 2

In another example, the calibration check procedure may be applied to a wavefront sensor. A wavefront sensor, also referred to as an aberrometer (which term will be used interchangeably herein), is a device that measures a difference in the optical path of light between a deformed wavefront and an ideal, or reference, wavefront. The measurement, when properly processed, yields values for various aberrations in the optical system that the light propagates through, and which deform the wavefront. Wavefront sensors are used in a variety of applications, including high-energy lasers, astronomical imaging, and measuring the aberrations of the eye with the goal of improving visual quality. One example of a wavefront sensor is the Shack-Hartmann type wavefront sensing instrument that can be used to measure, among other parameters, higher-order ocular aberrations.

Figure 6:
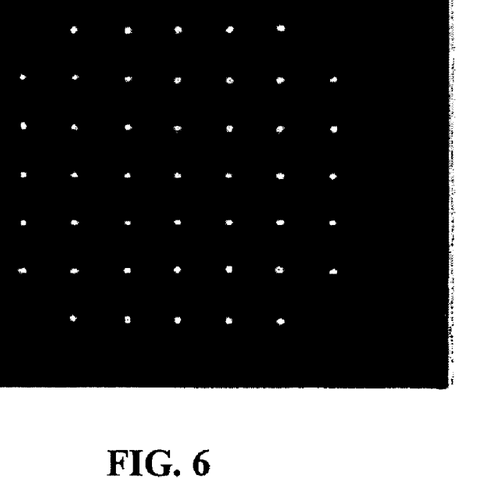
FIG. 6 is an example of a raw image of a calibration test tool used to calibrate a wavefront sensor.

To calibrate the wavefront sensor, centroid images of test tools are analyzed and the calibration values are saved in the calibration data. An example of a raw image of a test tool used to calibrate the wavefront sensor is given in FIG. 6. The raw images are saved as digital raw data sets during step 300. The recognized positions of the centroids in combination with the focal length of the lenslet array (f) and the related pitch of the lenslet array determine the outcome of such a Hartmann-Shack sensor. The lenslet array parameters are examples of calibration parameters that could be overwritten by wrong values during a software upgrade.

Figure 7:
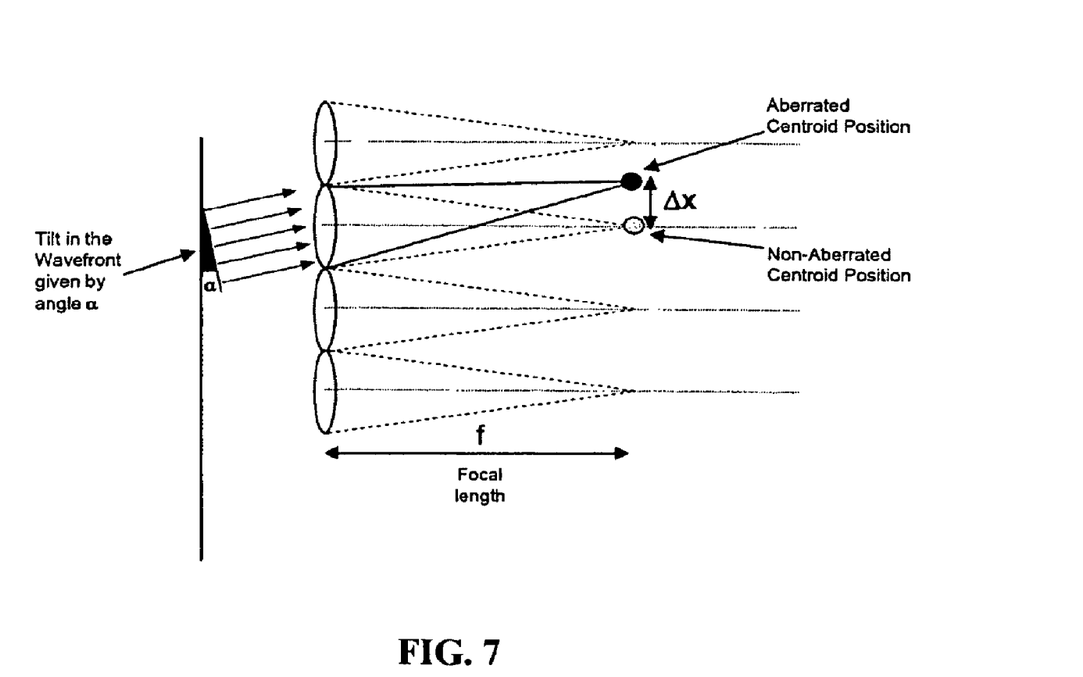
FIG. 7 is an illustration of one example of a wavefront sensor lenslet array, according to aspects of the invention.

For example, referring to FIG. 7, there is illustrated a diagram of one example of a wavefront sensor, showing the relationship between values calculated during analysis of the stored raw data and system calibration parameters. A wavefront sensor such as discussed in this example measures the tilt of the wavefront or in other words the angle ($\alpha$) of the wavefront propagating through the system. The tilt in the wavefront leads to a spatial shift ($\Delta x$) of the focused bundle of light rays which propagates through the lenslet array and generates the centroid image. The tilt of the wavefront ($\alpha$) or the tangent of this angle (tan [$\alpha$]) has a direct relation to the measured displacement ($\Delta x$) and the focal length of the lenslet array (f), as given by the following equation:

$$\tan(\alpha) = \frac{\Delta x}{f} \quad (2)$$

Accordingly, in one example, a remote calibration check of the wavefront sensor can be used to verify the calibration parameter that defines the focal length of the lenslet array (f). In another example, the remote calibration check may also be used to verify the calibration parameter that defines the camera pixel to millimeter adjustment factor as the calculated displacement value ($\Delta x$) is dependent on the pixel to millimeter adjustment factor.

Figure 8:
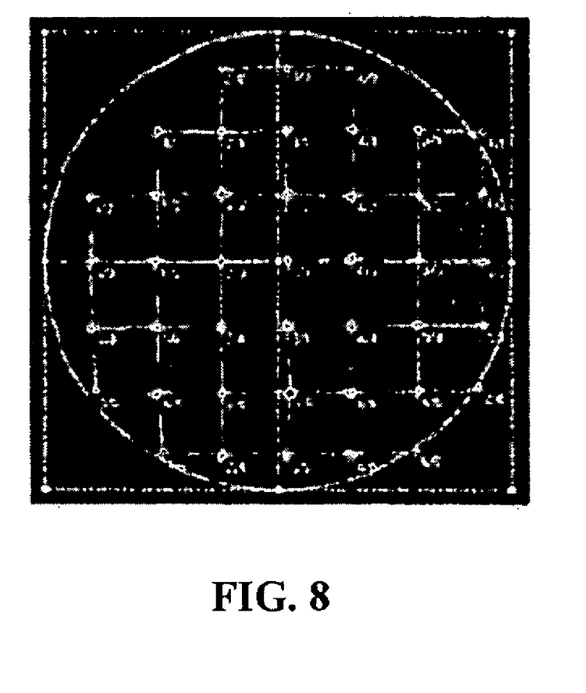
FIG. 8 is an example of a processed image corresponding to the raw image of FIG. 6.

In one example, for a remote calibration check of the wavefront sensor, in step 401, the raw Hartman-Shack images (FIG. 6) of calibration spheres are reloaded into the processing stream. The processing software analyses the raw images and calculates the diagnostic reading (step 420). In one example, the diagnostic reading can include a tilt angle ($\alpha_{act}$). Having a nominal tilt angle $\alpha_{nom}$ given as the target value, any deviation in the actual determined angle $\alpha_{act}$ will indicate a deviation of either the system calibration parameter f or the determined value $\Delta x$ which, as discussed above, is itself dependent on the camera calibration factor Pix2 mm. Thus, in step 430, the processing software which checks the diagnostic reading against defined acceptance criteria may check the determined angle $\alpha_{act}$ against the nominal tilt angle $\alpha_{nom}$ to determine whether or not the calibration status of the wavefront sensor is valid. FIG. 8 is an example of a processed image, obtained following step 420, corresponding to the raw image illustrated in FIG. 6. As discussed above, following step 430, a calibration status indicator is generated, indicating either that the calibration status of the wavefront sensor is operational (step 440) or non-operational (step 450), and is saved on the computer 220, transmitted to the remote user interface 230, and/or locally displayed by the computer 220. In one example, in step 450, the calibration status indicator may indicate an error in either one of the calibration parameters f or Pix2 mm, as discussed above.

EXAMPLE 3

In another example, the calibration check procedure may be applied to a topographer, such as, for example, the Orbscan™ device available from Bausch and Lomb, Inc. The Orbscan™ instrument is an example for a diagnostic system which incorporates two different modules in one system, namely a placido device and a slit scan device. The calibration check procedure can be used to remotely verify the calibration status of one or both of these modules.

Figure 9:
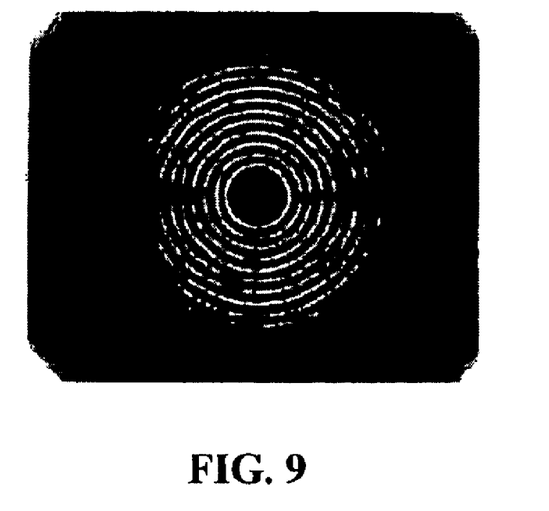
FIG. 9 is an example of a reference placido image.
Figure 10:
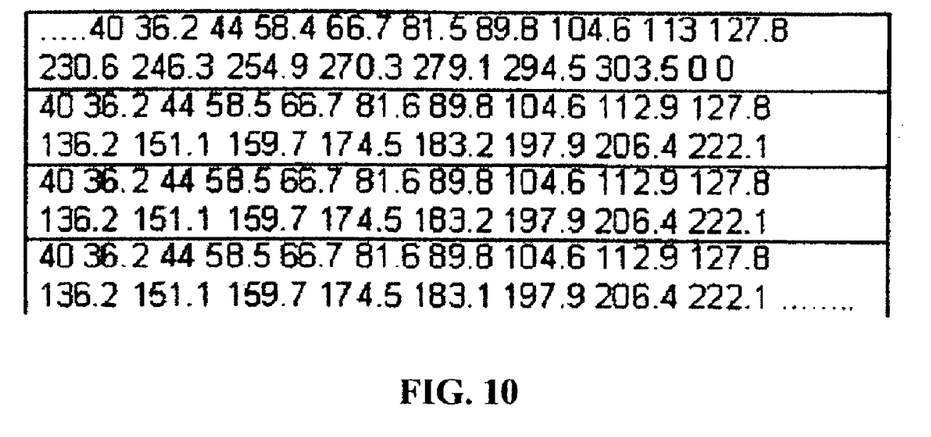
FIG. 10 is a portion of a table illustrating exemplary stored raw calibration test data corresponding to the placido image of FIG. 9.
Figure 11:
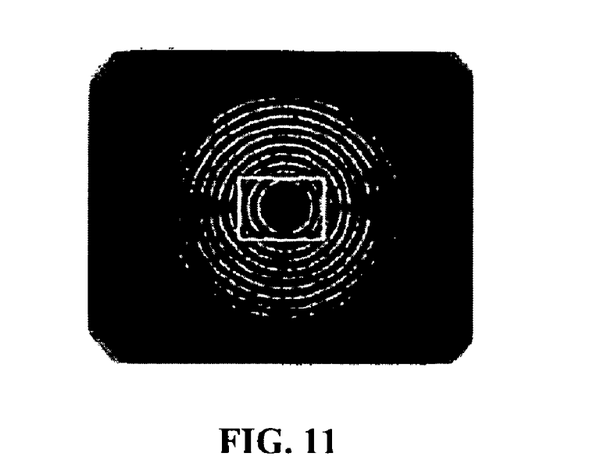
FIG. 11 is an example of a reference placido image used for gain analysis of a placido device.

The placido device is calibrated using a reference sphere having defined dimensions. During calibration, a reference placido image, such as that illustrated in FIG. 9, of the defined reference sphere. The ring positions of the reference sphere are evaluated and stored during step 300. FIG. 10 illustrates an example of the stored raw digital calibration test data corresponding to the reference image of FIG. 9. Additionally the gain of the camera can analyzed and checked with the acquired placido image. FIG. 11 illustrates an example of a reference placido image for gain analysis.

To perform a remote calibration check of the placido device, the raw calibration test data (FIG. 10) corresponding to the raw placido images (FIG. 9) of the calibration sphere are loaded into the processing steam (step 410). The processing software analyzes the images (data) and calculates the related parameters to generate the diagnostic reading (step 420). The diagnostic reading then compared with defined acceptance criteria (step 430) to determine whether or not the calibration status of the module is valid. Similarly, to check the gain of the camera, the reference image (FIG. 11) is analyzed and the resulting gain measurement is compared with pre-defined ideal gain values.

Figure 12A:
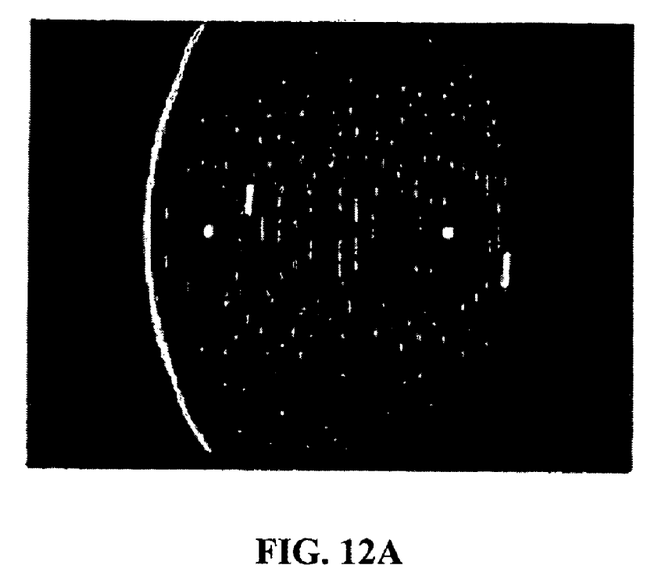
FIG. 12A is an example of a slit image of a reference sphere with a defined radius.
Figure 12B:
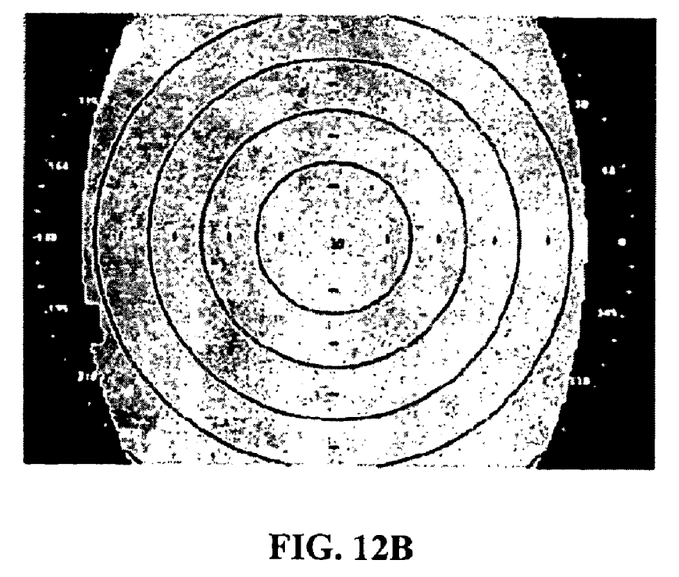
FIG. 12B is an example of an anterior elevation map of the reference sphere.

To calibrate the slit scan device, multiple slit images which are acquired during one acquisition are analyzed. The detected edges of the slits are visually checked for disturbance. If the slits show no inconsistencies, the elevation of the anterior surface is analyzed and the results compared to an acceptance window. An example of a raw slit image and a related elevation map resulting from the processing of the raw image are shown in FIGS. 12A and 12B, respectively.

To perform a remote calibration check of the slit scan device, the raw slit images of the calibration sphere (FIG. 12A) are uploaded into the processing stream (step 410). The images are analyzed and the related diagnostic reading calculated (step 420). As discussed above, the diagnostic reading is compared to a known correct nominal reading (step 430) and a calibration status indicator is generated. In one example, the calibration status indicator may combine the results from the calibration check of both the placido device and the slit scan device to indicate whether or not the calibration status of the topographer as a whole is valid. Alternatively, the calibration status indicator may include individual indications as to whether or not the calibration statuses of the individual modules are valid.

The above examples illustrate how different instruments as well as the various subsystems of a complex diagnostic system can be remotely checked for appropriate software calibration. As will be appreciated by those skilled in the art given the benefit of this disclosure, embodiments of the calibration check procedure may be applies to any kind of diagnostic system which is based on a type of image acquisition technology. In addition, non-image data streams may similarly be injected into the processing step of embodiments of the calibration check method to replicate other kinds of diagnostic data, such as, for example, an A-Scan generated by a partial coherence interferometer used for the determination of the eye length.

Having thus described several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A method of remotely updating and verifying a calibration status of an instrument that comprises a measurement portion and a computer system coupled to the measurement portion, the method comprising acts of:
   receiving a software update at the instrument from a remote location via a communications link;
   without activating the measurement portion of the instrument to measure a calibration object, using the software update to perform a calibration check procedure at the instrument; and
   using a processor to provide a calibration status indicator that identifies the calibration status of the instrument following the calibration check procedure.

2. The method as claimed in claim 1, wherein performing the calibration check procedure includes:
   retrieving stored raw calibration test data;
   processing the raw calibration test data using the software update and generating a diagnostic reading;
   comparing the diagnostic reading to a known correct nominal reading; and
   based on the comparison, generating the calibration status indicator.

3. The method as claimed in claim 2, wherein performing the calibration check procedure further comprises retrieving stored calibration parameters; and
   wherein processing the raw calibration test data is performed using the calibration parameters.

4. The method as claimed in claim 3, wherein generating the calibration status indicator includes generating the calibration status indicator that indicates that the calibration status of the instrument is non-operational.

5. The method as claimed in claim 4, wherein generating the calibration status indicator includes generating data that identifies a corrupted calibration parameter.

6. The method as claimed in claim 2, wherein generating the calibration status indicator includes generating a calibration status indicator that indicates that the calibration status of the instrument is operational.

7. The method as claimed in claim 2, wherein retrieving the stored raw calibration test data includes retrieving a stored digital image.

8. The method as claimed in claim 1, wherein providing the calibration status indicator includes providing the calibration status indicator from the instrument via the communications link.

9. A method of verifying a calibration status of an instrument, the method comprising acts of:
   receiving providing a software update at the instrument from a remote location;
   retrieving stored raw calibration test data;
   processing the raw calibration test data using the software update to generate a diagnostic reading;
   comparing the diagnostic reading to a known nominal reading; and
   based on the comparison, generating an output indicative of the calibration status of the instrument;
   wherein the verifying of the calibration status of the instrument is performed without measuring a calibration object with the instrument.

10. The method as claimed in claim 9, wherein retrieving the stored raw calibration test data includes retrieving a stored digital image.

11. The method as claimed in claim 10, wherein processing the raw calibration test data includes processing the raw calibration test data using calibration parameters specific to the instrument.

12. The method as claimed in claim 11, wherein generating the output indicative of the calibration status of the instrument includes generating an output that identifies a corrupted calibration parameter.

13. The method as claimed in claim 9, wherein generating the output indicative of the calibration status of the instrument includes generating an output that indicates instrument maintenance is required.

14. The method as claimed in claim 9, wherein generating the output indicative of the calibration status of the instrument includes generating an output that indicates that the instrument is properly calibrated.

15. A diagnostic system comprising:
   a measurement head;
   a storage device coupled to the measurement head that stores raw calibration test data generated by the measurement head; and
   a processor coupled to the storage device and configured to receive a software update, and without activating the measurement head of the instrument to measure a calibration object, obtain the stored raw calibration test data, process the raw calibration test data using the software update to generate a diagnostic reading, to compare the diagnostic reading to a known nominal reading, and based on the comparison, to generate an output indicative of a calibration status of the diagnostic system.

16. The diagnostic system as claimed in claim 15, further comprising a communications port coupled to a communications link and to the processor; and
   wherein the processor is further configured to transmit the output to a remote location via the communications link.

17. The diagnostic system as claimed in claim 16, wherein the processor is further configured to receive a software upgrade via the communications link and to initiate a calibration check procedure following installation of the software upgrade.

18. The diagnostic system as claimed in claim 15, wherein the diagnostic system comprises at least one of a pupilometer, a wavefront sensor, a placido device and a slit scan device.

19. The diagnostic system as claimed in claim 15, wherein the storage device stores calibration parameters specific to the diagnostic system; and
   wherein the processor is further configured to retrieve at least one calibration parameter from the storage device and to process the raw calibration test data using the at least one calibration parameter to generate the diagnostic reading.

20. The diagnostic system as claimed in claim 19, wherein the output indicates that the calibration status of the diagnostic system is invalid, and contains information identifying at least one corrupted calibration parameter.

21. The diagnostic system as claimed in claim 15, wherein the stored raw calibration test data includes a digital image of a calibration object.

* * * * *